US006856830B2

(12) United States Patent
He

(10) Patent No.: US 6,856,830 B2
(45) Date of Patent: Feb. 15, 2005

(54) METHOD AND APPARATUS OF THREE DIMENSION ELECTROCARDIOGRAPHIC IMAGING

(76) Inventor: Bin He, 121 Franklin Ave., River Forest, IL (US) 60305

( * ) Notice: Subject to any disclaimer, the term of this patent is extended or adjusted under 35 U.S.C. 154(b) by 356 days.

(21) Appl. No.: 09/909,338

(22) Filed: Jul. 19, 2001

(65) Prior Publication Data

US 2003/0018277 A1 Jan. 23, 2003

(51) Int. Cl.$^7$ ........................................... A61B 5/0402

(52) U.S. Cl. ...................................................... 600/513

(58) Field of Search ............................... 600/508, 509, 600/512–513, 515–519, 544, 300–301; 128/920, 922, 924–925

(56) References Cited

U.S. PATENT DOCUMENTS

| | | | | |
|---|---|---|---|---|
| 4,736,751 A | * | 4/1988 | Gevins et al. | 600/545 |
| 5,263,488 A | * | 11/1993 | Van Veen et al. | 600/544 |
| 5,273,038 A | * | 12/1993 | Beavin | 600/416 |
| 5,307,807 A | * | 5/1994 | Valdes Sosa et al. | 600/409 |
| 5,331,970 A | * | 7/1994 | Gevins et al. | 600/544 |
| 5,546,951 A | * | 8/1996 | Ben-Haim | 600/515 |
| 5,594,849 A | * | 1/1997 | Kuc et al. | 345/632 |
| 5,687,724 A | * | 11/1997 | Jewett et al. | 600/409 |
| 5,687,737 A | * | 11/1997 | Branham et al. | 600/523 |
| 5,701,909 A | * | 12/1997 | Amir et al. | 600/544 |
| 6,073,040 A | * | 6/2000 | Kiyuna | 600/409 |
| 6,240,307 B1 | * | 5/2001 | Beatty et al. | 600/374 |
| 6,330,470 B1 | * | 12/2001 | Tucker et al. | 600/544 |
| 6,370,412 B1 | * | 4/2002 | Armoundas et al. | 600/373 |
| 6,400,981 B1 | * | 6/2002 | Govari | 600/509 |

OTHER PUBLICATIONS

Savard et al., "Representation of cardiac electrical activity by a moving dipole for normal and ectopic beats in the intact dog," Circulation Research, 425, 1980.

Mirvis et al., "Detection and localization of multiple epicardial electrical generators by a two–dipole ranging technique," Circulation Research, 551, 1977.

Barr et al. , "Relating epicardial to body surface potential distributions by means of transfer coefficients based on geometry measurements," IEEE Transactions on BME, 1, 1977.

Oster et al., "Noninvasive electrocardiographic imaging: reconstruction of epicardial potentials, electrograms, . . . " Circulation, 1012, 1997.

Ben–Haim et al. , "Nonfluoroscopic in vivo navigation and mapping technology," Nature Medicine, 1393, 1996.

Khoury et al., "Three–dimensional electrophsyiological imaging of the intact canine left ventricle using a noncontact multielectrode cavitary probe . . . " Circulation, 399, 1998.

(List continued on next page.)

Primary Examiner—Kennedy Schaetzle
Assistant Examiner—Kristen Droesch Mullen

(57) ABSTRACT

An instrument and method for imaging and localizing of electrical activities in a biological system, comprising a plurality of sensors for detecting signals over a part of a surface of the biological system, a data acquisition unit for collecting the signals, a positioning device for determining positions of the sensors, a procedure for determining geometry information of the biological system, an electrical source model incorporating physical and physiological properties of the biological system, an estimator for determining the parameters of the electrical source model, and a unit for displaying the reconstructed excitation sequence and/or electrical source distribution in the three dimension space of the biological system and over time.

20 Claims, 5 Drawing Sheets

OTHER PUBLICATIONS

R.D. Pascual–Marqui et al., "Low resolution electromagnetic tomography: a new method for localizing electrical activity in the brain," Int. J. of Psychophysiology, 49, 1994.

D. Yao and B. He "The Laplacian weighted minimum norm estimate of three dimensional equivalent charge distribution in the brain," Proc. of IEEE–EMBS, 2108, 1998.

I. F. Gorodnitsky et al., "Neuromagnetic source Imaging with FOCUS: a recursive weighted minimum norm algorithm," Electroencepholography & Clinical Neurophysiolog, 231, 1995.

Lu et al., "Extraction of implicit information in biosignals," Method of Information in Medicine, 332, 1997.

* cited by examiner

METHOD AND APPARATUS OF THREE DIMENSION ELECTROCARDIOGRAPHIC IMAGING

This invention was made with Government support under grant BES 9875344 by the National Science Foundation. The Government has certain rights in the invention.

FIELD OF THE INVENTION

This invention relates to instruments and methods for imaging and localizing electrical events in a biological system.

BACKGROUND OF THE INVENTION

Noninvasive imaging of cardiac electrical activity inside the human body has historically been a challenge. A significant amount of effort has been put forth in past decades in the development of high-resolution cardiac electric imaging techniques, which attempt to image myocardial electrical activity without ad hoc assumption on the number of sources. Due to the high temporal resolution inherent in the bioelectromagnetic measurements such as electrocardiogram and magnetocardiogram, the availability of bioelectromagnetic source imaging modalities provides much needed high temporal resolution in mapping the functional status of the heart, and aiding clinical diagnosis and treatment of cardiac abnormalities, such as guiding catheter ablation of cardiac arrhythmias.

Attempts have been made to mathematically reconstruct the equivalent source distribution of cardiac bioelectric activity. The choice of equivalent cardiac source determines what kind of information that may be deduced concerning cardiac electrical source distribution. Savard et al. has approximate cardiac electrical activity by a single equivalent current dipole which can move within the myocardium, see "Representation of cardiac electrical activity by a moving dipole for normal and ectopic beats in the intact dog," Circulation Research, 425, 1980. However, Savard et al.'s approach did not provide a means of imaging distributed cardiac electrical activity but a single equivalent dipole. Mirvis et al. has attempted to localize multiple epicardial events using a two-dipole technique, see "Detection and localization of multiple epicardial electrical generators by a two-dipole ranging technique," Circulation Research, 551, 1977. However, Mirvis et al.'s approach also did not provide a means of imaging distributed cardiac electrical activity but only two discrete point sources within the heart. In an attempt to image distributed cardiac electrical activity, Barr et al. used the electrical potential over the outer surface of the heart as an equivalent source model, see "Relating epicardial to body surface potential distributions by means of transfer coefficients based on geometry measurements," IEEE Transactions on Biomedical Engineering, 1, 1977. However, Barr et al.'s approach provided electrical potential distribution over the two dimensional surface of the epicardium. Oster et al has further extended the technique to reconstruct epicardial potentials, electrograms and activation sequence, see "Noninvasive electrocardiographic imaging: reconstruction of epicardial potentials, electrograrns, and isochrones and localization of single and multiple electrocardiac events," Circulation, 1012, 1997. While Oster et al.'s approach provided activation sequence over the two dimensional surface of the epicardium, it did not provide a means of imaging cardiac activation sequence within the three dimensional volume of the heart. Branham et al. described a system of mapping activation sequence over the epicardial and endocardial surfaces, see U.S. Pat No. 5,687,737. However, these heart surface activation imaging approaches only provided activation sequence over the heart surface, not within the three dimensional volume of the myocardium.

Attempts have also been made to map and localize cardiac electric activity from the endocardium due to rapid development in catheter techniques. Ben-Haim et al. has developed a non-fluorescent electroanatomic catheter mapping technique using electromagnetic guidance of the catheter positioning, see "Nonfluoroscopic in vivo navigation and mapping technology," Nature Medicine, 1393, 1996. However, due to the multiple sequential positioning and measurement of the potentials, this technique currently does not provide beat-to-beat mapping capability, which is required for guiding catheter ablation of hemodynamically unstable arrhythmia. Khoury et al. has attempted to use a cavitary noncontact multielectrode catheter-probe to record electrical potentials in the blood-filled cavity, and explored inverse reconstruction of endocardial potentials from the potential measurements made on the catheter probe, see "Three-dimensional electrophsyiological imaging of the intact canine left ventricle using a noncontact multielectrode cavitary probe: study of sinus, paced, and spontaneous premature beats," Circulation, 399, 1998. Beatty et al. described a system mapping electrical activity of the heart from endocardial surface, see U.S. Pat. No. 6,240,307. However, these approaches are invasive techniques, and the estimated electrical potential or activation patterns are over the two dimensional surface of endocardium, not within the three dimensional volume of the heart.

While the heart-surface inverse solutions provide much enhanced spatial resolution regarding the underlying cardiac electrical activity as compared with the smeared body surface (or balloon surface) potential distribution, the heart-surface inverse solutions are still limited in that it is an inverse solution over the surface of the heart, within which the true myocardial electric activity is located over the three-dimensional myocardium. For example, it is desirable to localize sites of origin of cardiac arrhythmia in the three-dimensional myocardium, in order to accurately guide radio-frequency catheter ablation procedures. The information available over the heart surface regarding the underlying myocardial activation will still need to be processed to lead to directly useful information in a clinical setting. There is a need to develop noninvasive techniques to image and localize cardiac electric activity and site of arrhythmias in the three-dimensional myocardium.

Recently attempts have been made to estimate the three-dimensional distribution of current dipoles not in the heart but in the brain through a Laplacian weighted minimum norm solution. See "Low resolution electromagnetic tomography: a new method for localizing electrical activity in the brain," published by R. D. Pascual-Marqui et al. in Int. J. of Psychophysiology, 49, 1994. See also "The Laplacian weighted minimum norm estimate of three dimensional equivalent charge distribution in the brain," published by D. Yao and B. He in the Proceedings of the $20^{th}$ annual international conference of IEEE engineering in medicine and biology society, 2108, 1998. The main advantage of these weighted minimum norm brain-imaging approaches is that knowledge of the source multiplicity is not required, and it may lead to estimates of the source density all throughout the three dimensional volume of the brain. I. F. Gorodnitsky et al. further improved the weighted minimum norm solution for localization of focal neural sources from magnetoencephalogram, using a recursive weighting strategy, see "Neuromagnetic source imaging with FOCUSS: a recursive weighted minimum norm algorithm," published in Electroencephology & clinical Neurophysiology, 231, 1995. However, there has been no, to our knowledge, prior art in estimating excitation sequence of neuronal activation within the three-dimensional volume of the brain. Amir et al. described a method and means of estimating brain source generators using a lead-field analysis method in a boundary element model of the head, see U.S. Pat. No. 5,701,909. However, Amir et al. did not show estimating three dimensional activation sequence within the brain. Tucker et al. also described a device of estimating brain electrical source, see U.S. Pat. No. 6,330,470. However, Tucker et al. also did not describe estimation of three dimensional activation sequence within the brain. Jewett et al. showed a device for measuring variations in measured physical parameters of source-generators, see U.S. Pat. No. 5,687,724. However, Jewett et al. also did not determine the activation sequence within the brain. Van Veen et al. described a method of estimating brain electrical sources by filter banks, see U.S. Pat. No. 5,263,488. However, Van Veen et al. also did not show estimating activation sequence within the brain.

To our knowledge, there have been no comprehensive reports to estimate the three-dimensional excitation sequence, three dimensional distribution of electrical source inside the heart from noninvasive electrocardiographic measurements made over the body surface or magnetocardiographic measurements made out of the body. There have been, to our knowledge, no comprehensive reports to estimate the activation sequence within the three dimensional volume of the brain from the electrical signals measured over the surface of the head or magnetoencephalograms measured out of the head. Lu et al attempted to localize the site of preexcitation of WPW syndrome using a model based inverse procedure, see "Extraction of implicit information in biosignals," published in Methods of Information in Medicine, 332, 1997. However, Lu et al. did not show determining the three dimensional activation sequence throughout the myocardial volume, did not show determining the three dimensional distribution of transmembrane potentials or electrical potentials within the myocardial volume, did not show determining the three dimensional distribution of current dipole or monopole sources within the myocardial volume.

However, in the prior art, no descriptions have been given on imaging cardiac electric source distribution within the three dimensional space of the heart using weighted minimum norm approaches. No descriptions have been given to estimate and image the activation patterns in the three dimensional myocardium. Further innovation in the three-dimensional cardiac electrical source imaging and in three-dimensional cardiac activation imaging is much needed.

Similarly, in the prior art, no descriptions have been given on estimating activation sequence within the brain by incorporating a three dimensional brain activation model into the inverse process. Innovation in the three dimensional brain imaging by using an activation model will advance state of the art in brain source imaging.

SUMMARY OF THE INVENTION

While the present invention is described with respect to biological systems, it can be understood that the teachings apply to nonbiological systems as well, in which distributions of sources and/or excitation patterns can be imaged within a volume from measurements made at a surface.

In accordance with the present invention, an imaging instrument for imaging of bioelectrical sources within the organ systems of a biological system comprises means of collecting biosignals over a part of a surface inside or outside of the body of a biological system, means for determining positions of the sensors, means for determining geometric information of the body of a biological system, means for estimating electrical sources and/or activation patterns within the organ systems using a spatial distribution of current dipoles or monopoles occupying the three dimension of organ systems, means for estimating electrical sources and/or activation patterns within the organ systems using computer source models embedding physiological a priori knowledge on the physiological activation process of the organ systems, and means for displaying the estimated activation patterns and/or source distribution over the three dimension of organ systems, means for displaying the collected biosignals in both time domain and space domain together with the estimated activation sequence or source distribution, and means for displaying the estimated electrical sources and/or activation patterns, together with other images of the organ systems including magnetic resonance imaging and computer tomography.

In accordance with one aspect of the present invention, an imaging instrument for imaging of bioelectrical sources within the heart of a biological system comprises means of collecting biosignals over a part of a surface inside or outside of the body of a biological system, means for determining positions of the sensors, means for determining geometric information of the body of a biological system, means for estimating activation sequence and/or electrical sources within the heart using a spatial distribution of current dipoles or monopoles occupying the three dimensional myocardium, means for estimating activation sequence and/or electrical sources within the heart using heart-computer-models incorporating physiological a priori information, and means for displaying the estimated activation sequence and/or source distribution over the three dimension of heart, means for displaying the collected biosignals in both time domain and space domain over or out of the body surface, together with the estimated activation sequence or source distribution within the heart, and means for displaying the estimated activation sequence and/or electrical source distribution within the heart together with other imaging results including magnetic resonance imaging and computer tomography.

This aspect of the invention further relates to methods wherein body surface electrocardiographic potentials are measured using electrodes, and the electrode positions are determined, and the heart-torso geometry information is determined from magnetic resonance imaging or computer tomography imaging, and cardiac activation sequence and/or electrical source distributions are estimated from body surface electrocardiographic potentials and the heart-torso geometry information, using three dimension heart source models of physical properties or physiological properties, and estimated cardiac activation sequence and/or source distribution are displayed over the three dimension myocardium, with or without displaying of other imaging results including magnetic resonance imaging and computer tomography.

This aspect of the invention further relates to using of heart-source model in which a priori information regarding physiological and pathophysiological processes is incorporated into by means of cellular automaton models with cellular action potentials being determined, excitation rules governing the activation within the heart, and inhomogeneity and anisotropy properties of the heart-torso tissues are taken into consideration in the heart and torso computer model. This aspect of the invention further relates to the heart source model in which cellular action potentials are determined by solving differential equations of a membrane patch, including variables of transmembrane ionic currents.

One aspect of the invention relates to means and methods for guiding catheter ablation of a part of the heart or other electrically active organs. This invention can be utilized to help identify the ablation site, for example, in order to prevent or manage ventricular tachycardia or atrial flutter. In accordance with this aspect of the invention, a catheter is further utilized to explore the vicinity of the potential source areas where abnormalities may originate, to confirm and finalize the ablation site, and radio-frequency energy is delivered onto the identified site.

One aspect of the invention further relates to methods wherein scalp electroencephalographic signals are measured using electrodes, and the electrode positions are determined, and the head-brain geometry information is determined from magnetic resonance imaging or computer tomography imaging, and brain activation sequence is estimated from scalp potentials and the head-brain geometry information, using brain source models in which cell action potentials, excitation rules and inhomogeneity properties of the brain are considered, and estimated brain activation sequence are displayed over the three dimension brain, with or without displaying of other imaging results including magnetic resonance imaging and computer tomography.

In accordance with one aspect of the present invention, an imaging instrument for imaging of bioelectrical sources within the heart of a biological system comprises means of collecting magnetocardiographic signals over a part of a surface outside of the body of a biological system, means for determining positions of the sensors, means for determining geometric information of the body of a biological system, means for estimating activation sequence and/or electrical source distributions within the heart using a spatial distribution of current dipoles or monopoles occupying the three dimensional myocardium, means for estimating activation sequence and/or electrical source distributions within the heart using heart-computer-models incorporating physiological a priori information, and means for displaying the estimated activation sequence and/or source distribution over the three dimension of heart with or without displaying of other imaging results including magnetic resonance imaging and computer tomography, and means for displaying the collected magnetocardiographic signals in both time domain and space domain out of the body. surface, together with the estimated activation sequence or source distribution within the heart.

This aspect of the invention also relates to means and methods for imaging of cardiac activation sequence and/or source distribution within the heart by using a heart-source model from bioelectric and biomagnetic signals collected by multi-electromagnetic sensors.

The present invention provides a new method of imaging of cardiac activation and/or distributed cardiac source distribution in three dimensional myocardium, by means of a three-dimension heart source model embedding physical or physiological properties. This feature of the present invention may enable it to become an important tool guiding clinical diagnosis and management of disorders in the heart and other organ systems.

BRIEF DESCRIPTION OF THE DRAWINGS

FIG. 2A and FIG. 2B illustrate distribution of the cardiac current density over slices of the ventricles from the base to the apex (from left to right, and from top to bottom).

DETAILED DESCRIPTION OF THE INVENTION

Figure 1:
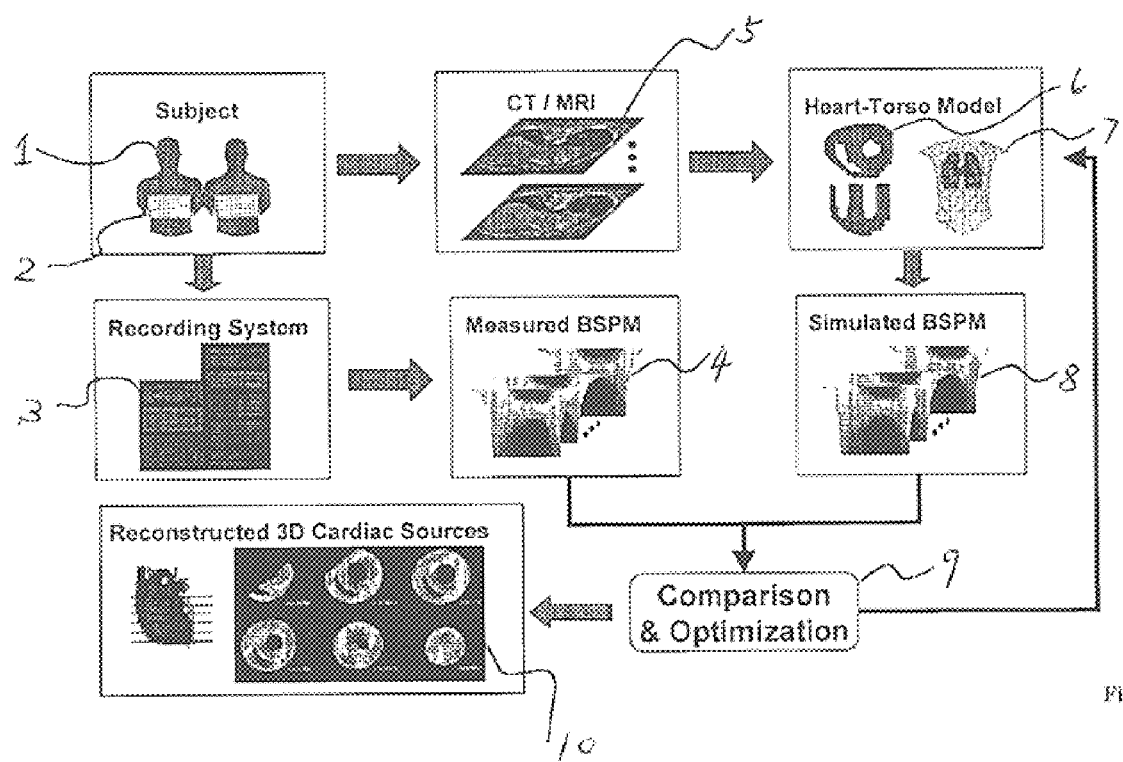
FIG. 1 is an embodiment of the present invention for imaging of three dimensional activation patterns in the myocardium from body surface electrocardiograms, geometry information of the heart and torso, and a heart-source-model.

Since the electrical signals are measured at remote positions over the body surface from their biological origins, they are essentially summed responses from a number of active biological cells inside the body. The method of the present invention invokes an engineering method to reconstruct activation patterns and bioelectrical source distribution within the heart and other organ systems from bioelectromagnetic signals measured over the body surface, by means of a computer heart source model.

In accordance with the present invention, a heart-source-model based imaging is performed. The biosignals are collected by a plurality of sensors. The biosignals are then passed through a filter to remove noise from the biosignals. The geometry of the heart and torso is further obtained from magnetic resonance imaging or computer tomography, and a heart-torso geometry model is constructed. The heart is divided into a plurality of segments, at each of which an equivalent current dipole or monopole is assigned. Then we have the following mathematical model, which relates the heart source distribution inside the myocardium to the biosignals over or out of the body surface:

$$V = AX \tag{1}$$

where V is the vector consisting of m biosignals, X is the unknown vector of source strengths, which are located at n sites covering the entire myocardium, and A is the transfer matrix. The measurement at each sensor is produced by a linear combination of all source components, with columns of A as weighting factors. Equation (1) is a heavily under-determined system because, in general, the number of source elements inside the myocardium greatly exceeds the number of sensors. A solution is to use the weighted minimum norm strategy as follows:

$$X = (W L^T L W)^{-} A^T (A (W^T L W)^{-} A^T)^{+} V \tag{2}$$

where W is a diagonal matrix with $w_{ii} = \|A_i\|$, and $A_i$ is the i-th column of A. L may be a Laplacian operator, a unit matrix, or another matrix. − denotes the inverse of a matrix, and + denotes the general inverse of a matrix.

In accordance with a preferred embodiment, the invention uses a recursive weighting algorithm. The recursive weighting algorithm finds localized solutions by starting with the weighted minimum norm estimate of cardiac sources. In each iteration step, the weighting matrix $W_k$ is updated by taking the product of $W_{k-1}$ with the diagonal current matrix from the preceding step:

$$W_k = W_{k-1} \cdot \mathrm{diag}(X_1^{k-1} X_2^{k-1} \ldots X_n^{k-1}) \qquad (3)$$

Each diagonal element of W corresponds to one element of the source. Large elements of W in conjunction with the data make the corresponding elements in X large and vice versa for small elements. The process continues until most elements are reduced to zero. This preferred embodiment is useful for localizing and imaging the site of initial activation and origin of cardiac arrhythmia.

In accordance with a preferred embodiment, the invention uses current dipoles to equivalently represent the regional myocardial activity, as the source elements. In other words, X consists of n dipoles, each has 3 components.

In accordance with another preferred embodiment, the invention uses current monopoles to equivalently represent the regional myocardial activity, as the source elements.

In other words, X consists of n monopoles, each has only one component.

In accordance with another preferred embodiment, the invention uses electric potentials as the source elements of vector X, which will lead to reconstruction of electric potentials in the three dimension of myocardium.

In accordance with another preferred embodiment, the invention further derives the activation patterns within the myocardium from the estimated distributions of current dipoles, current monopoles, or electric potentials.

In accordance with another preferred embodiment, the invention uses a heart-source-model in which physiological or pathological a priori information is embedded to represent cardiac electrical activity. Such physiological heart-model may be cellular automaton model, or rule-based propagation heart model, or other heart models in which properties of physiological and pathophysiological processes are taken into account. A preliminary diagnosis system is used to determine cardiac status based on a priori knowledge and the measured biosignals. The output of the preliminary diagnosis system provides the initial heart model parameters used in the optimization system. Then the body surface potential maps (BSPMs) are simulated using the computer heart model, and then the objective functions that assess the similarity between the measured and simulated BSPMs are calculated. If the measured BSPM and the simulated BSPM matches well, the activation sequence produced by the heart model is regarded as the reconstructed activation sequence in the heart. Similarly heart model parameters corresponding with the heart activation or abnormalities are also used as characteristics guiding clinical diagnosis and intervention. If the measured BSPM. and the simulated BSPM do not match well, the heart model parameters are adjusted with the aid of the optimization algorithms and the simulation procedure proceeds until the objective functions satisfy the given convergent criteria.

In accordance with another preferred embodiment, the invention uses a brain-source-model in which physiological or pathological a priori information is embedded to represent brain electrical activity. Such physiological brain-source-model may be cellular automaton model, or rule-based propagation brain model, or other brain models in which differential equations are solved to determine cellular action potentials. Inhomogeneity properties of the brain may be included into such brain source models. A preliminary diagnosis system is used to determine brain status based on a priori knowledge and the measured biosignals. The output of the preliminary diagnosis system provides the initial brain model parameters used in the optimization system. Then the BSPMs are simulated using the computer brain model, and then the objective functions that assess the similarity between the measured and simulated BSPMs are calculated. If the measured BSPM and the simulated BSPM matches well, the activation sequence produced by the brain model is regarded as the reconstructed activation sequence in the brain. Similarly brain model parameters corresponding with the brain activation or abnormalities are also used as characteristics guiding clinical diagnosis and intervention. If the measured BSPM and the simulated BSPM do not match well, the brain model parameters are adjusted with the aid of the optimization algorithms and the simulation procedure proceeds until the objective functions satisfy the given convergent criteria.

FIG. 1 illustrates one preferred embodiment of the present invention. Electrocardiographic signals are sensed from a human subject 1 by a sensor array 2 with electrodes distributed uniformly or non-uniformly over the chest of the subject 1. The said signals are passed to a recording system 3, where the signals are amplified, band-pass filtered, A/D converted, and formed BSPMs 4. The positions of the sensors 2 may be measured by a positioning device. The geometry information of the heart and torso are determined using computer tomography (CT) or magnetic resonance imaging (MRI) 5, which is digitized to construct a finite element model of the heart 6 and a boundary (or finite) element model of the torso 7. In the heart finite element model, equivalent cardiac sources are either assigned as current dipoles or monopoles or electric potentials at each lattice within the heart model, or computed from assigned cardiac action potentials at each lattice based on propagation rules. The heart source model parameters may be initialized based on information extracted from measured BSPMs 4 using a preliminary diagnostic system, implemented by artificial neural networks (not shown in FIG. 1). BSPMs 8 are then simulated based on the heart-source-model 6 in the torso model 7. The measured BSPMs 4 and simulated BSPMs 8 are compared at unit 9 according to certain matching criteria such as the correlation coefficients between measured and simulated BSPMs, averaged over certain time epochs. When the measured BSPMs 4 and simulated BSPMs 8 match well, cardiac activation sequence 10 is reconstructed over the three dimensional myocardium. The optimized heart model parameters also provide other characteristics of physiological relevance.

EXAMPLE I

Figure 2A:
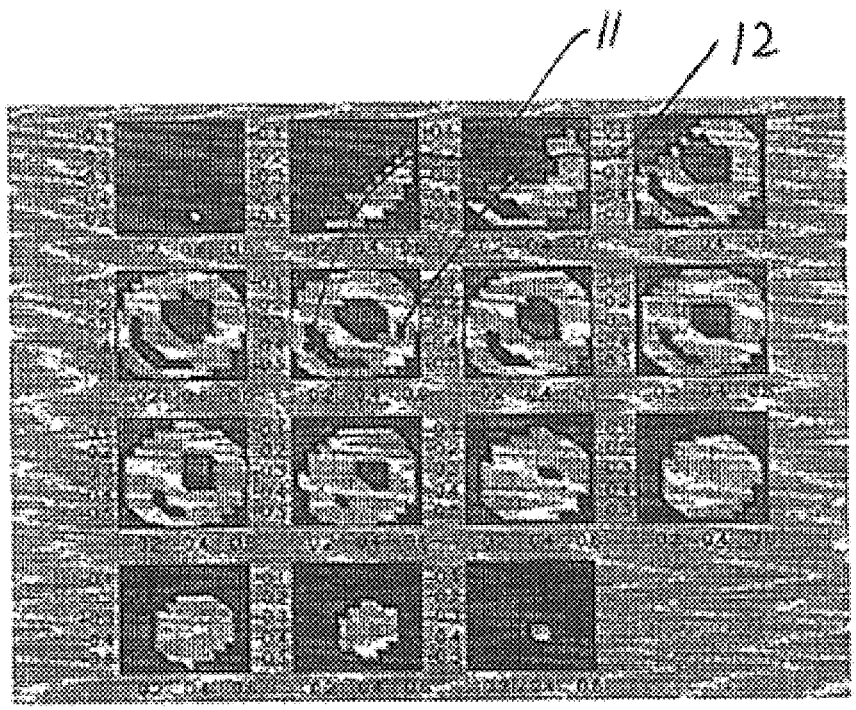
FIG. 2A and FIG. 2B illustrate an example of applying the present invention in imaging and localizing the focal ventricular sources.
Figure 2B:
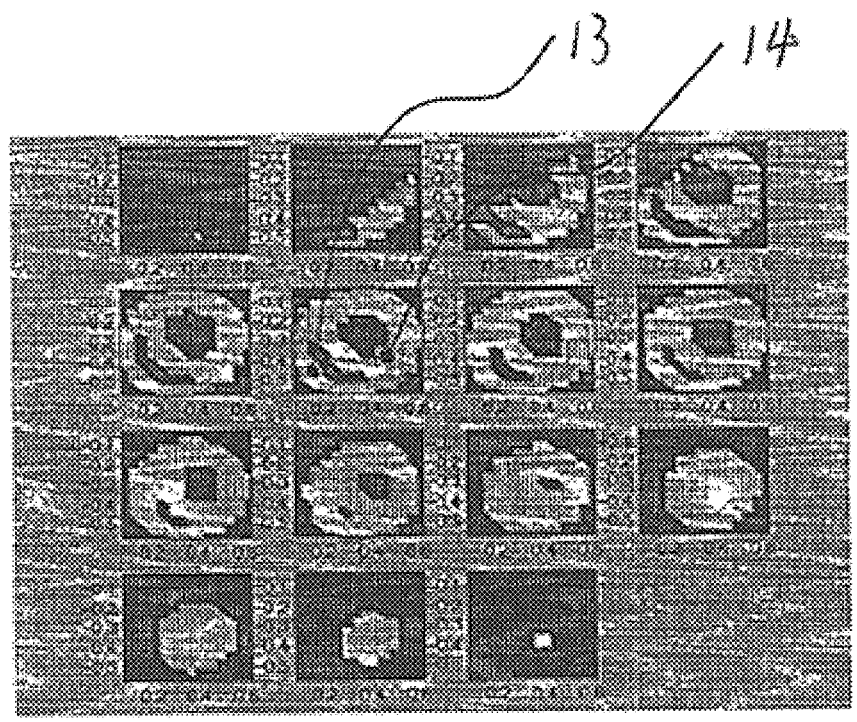

FIG. 2A and FIG. 2B illustrate an example of applying the present invention in localizing and imaging focal sources in the myocardium from body surface electrocardiographic potentials. A three-dimensional heart-torso inhomogeneous volume conductor model is used in this example. The ventricles are divided into an equi-distant lattice structure with an inter-lattice distance of 6.7 mm. In total there are 1,124 voxel nodes in the three dimension solution space of the ventricles. A current dipole located at the right ventricle 11 and a current dipole located at the left ventricle 12, both oriented from the waist towards the neck, are used to approximate well-localized myocardial electrical sources, as shown in FIG. 2A. Gaussian white noise of 5% is added to the calculated body surface potentials from assumed cardiac sources to simulate noise-contaminated body surface electrocardiographic potential measurements. The cardiac source distribution is approximated by a current dipole distribution consisting of 1,124 dipoles, located at each voxel within the ventricles. The orientations and strengths of the 1,124 current dipoles are estimated by means of the Laplacian weighted minimum norm algorithm with recursive weighting strategy, as described in the Section of Detailed Description of the Invention. After twenty iterations, the reconstructed cardiac sources are converged to two focal sites at the right and left ventricles, shown in FIG. 2B. One of the source localization results 13 is consistent with the "strue" dipole at the right ventricle, and another 14 is located at the left ventricular endocardium, shifted about 1 cm left of the "strue" dipole position. FIG. 2A and FIG. 2B illustrate the ability of the present invention to localize and image focal cardiac sources within the ventricles. Since no ad hoc assumption is made on the number of source dipoles, FIG. 2A and FIG. 2B illustrate the ability of the present invention to image and localize sites of initial activation, and sites of origin of arrhythmia from body surface electrocardiographic potentials and geoemtry informaiton of the heart-torso.

EXAMPLE II

Figure 3:
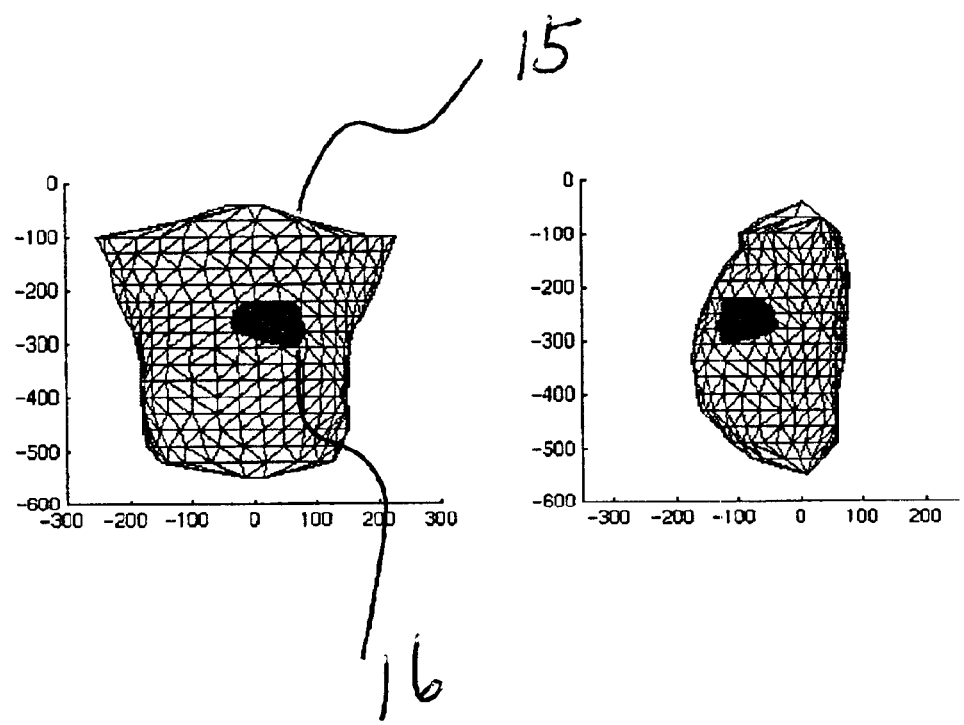
FIG. 3 illustrates another example of the heart-torso model constructed from a male human subject with ventricular pacemaker.
Figure 4:
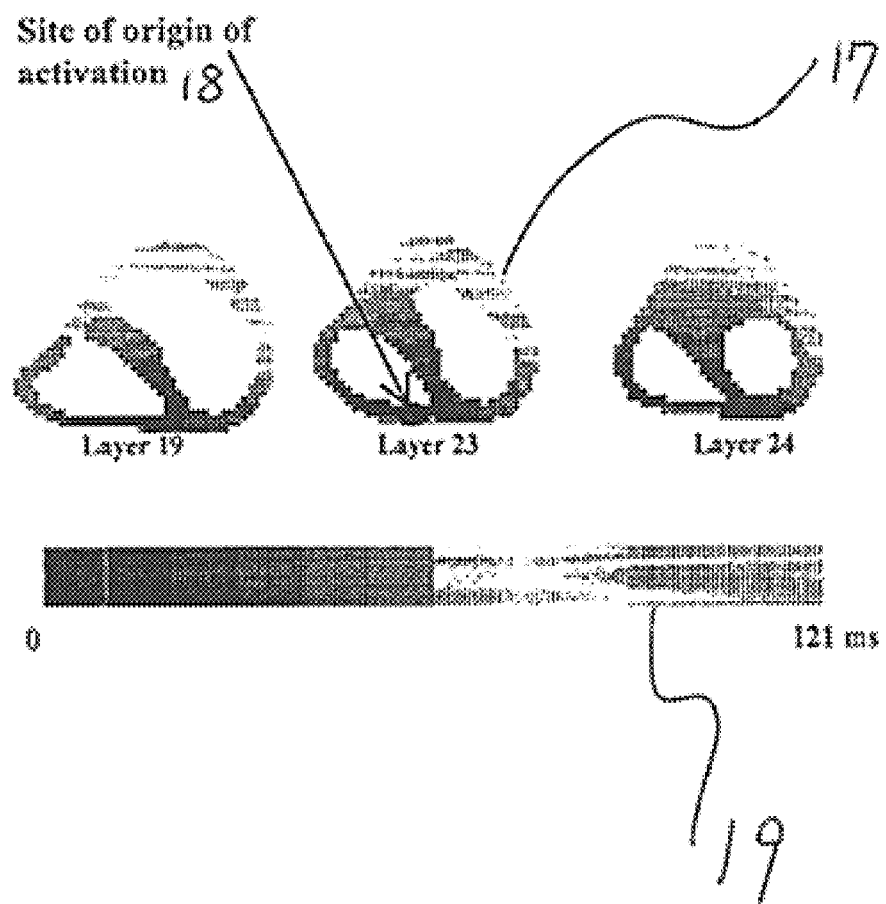
FIG. 4 illustrates the reconstructed activation patterns within the ventricles of a human subject, by means of the present invention. The site of origin of activation is localized from the activation map.
Figure 5:
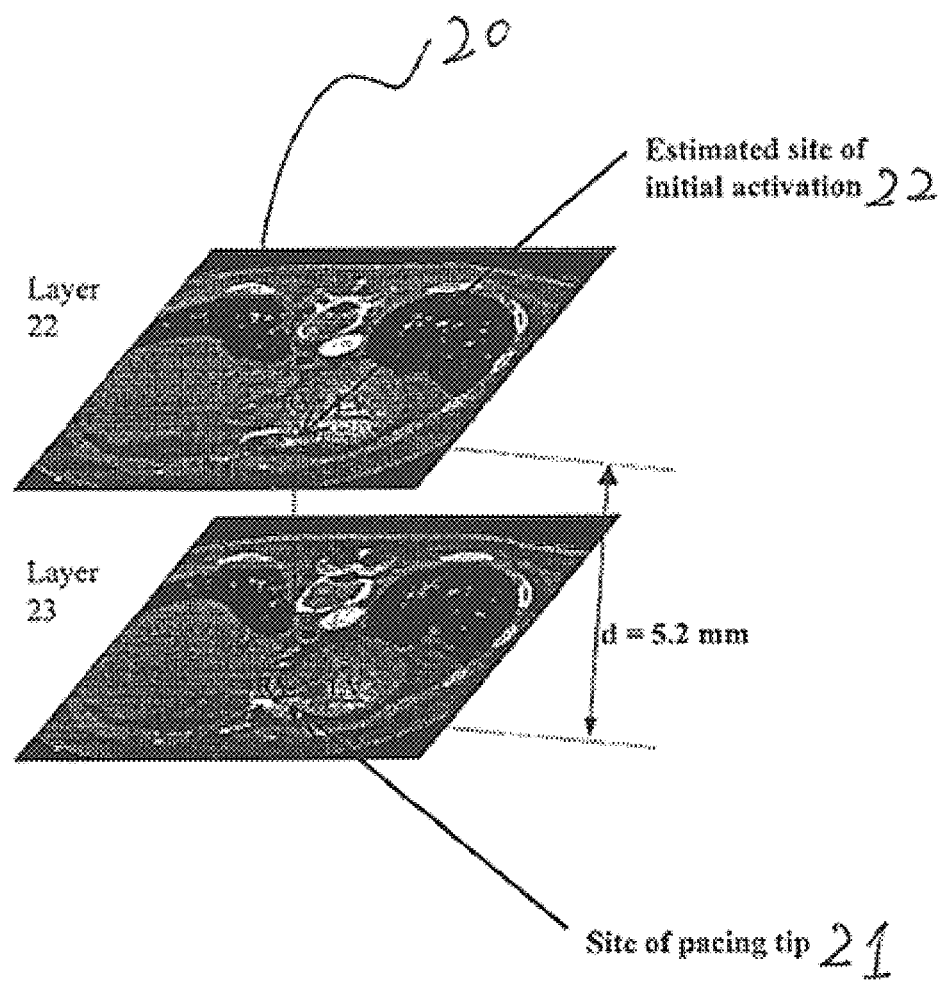
FIG. 5 illustrates the site of the pacemaker lead tip (bottom panel) and the site of the origin of activation (top panel), as displayed on ultrafast cardiac computer tomography image of the patient.

FIGS. 3–5 illustrate an example of applying the present invention in localizing and imaging site of origin of activation in the myocardium from body surface electrocardiographic potentials in a patient. FIG. 3 shows the boundary element torso model 15 and a finite element ventricle model 16 constructed from contrast and non-contrast ultrafast cardiac computer tomography scans of a male patient with a pacemaker. The realistic-geometry ventricle model 16 consists of 11,144 cubic myocardial cell units with grid resolution of 3 mm. The pacemaker lead tip is identified from the computer tomography images at the lower-anterior region of the right ventricle free wall and close to the septum. The BSPMs between 20 ms and 40 ms following pacing are recorded over 96 sites over the body surface, and used to reconstruct the activation sequence within the ventricles. FIG. 4 illustrates the estimated intracardiac activation patterns 17 at three different layers within the ventricle model 16, which best match the activation patterns corresponding to recorded body surface electrocardiograms, driven by the ventricular pacemaker. From FIG. 4, the site of origin of activation 18 is identified and localized from the activation patterns 17. The time of activation is shown in a scale 19. FIG. 5 illustrates the ultrafast cardiac computer tomography images of the subject 20. The site of the pacemaker lead tip 21 is illustrated in the lower image. The estimated site of initial myocardial activation 22 is shown in the upper image in FIG. 5. The distance between the site of lead tip 21 and the estimated site of initial activation 22 is 5.2 mm in this case. This example clearly demonstrates the capability of the present invention in reconsruting activation sequence within the three-dimension heart from body surface electrocardiograms and geometry information of the heart-torso, and in localizing the site of origin of cardiac activation in a clinical setting.

What is claimed is:

1. A method of imaging of electrical activities in a heart within a body comprising the steps of:
   (a) collecting signals over a part of a surface of the body, a part of the surface of the heart within the body, or a part of a surface out of the body, using a plurality of sensors and a data acquisition unit,
   (b) determining positions of the sensors,
   (c) determining geometry information of the heart within the body and of the torso,
   (d) constructing an electrical source model of the heart, which comprises a three dimension distribution of current dipoles or monopoles or electric potentials, or a computer heart model incorporating physiological a priori information that simulates the physiological and pathophysiological processes of the heart;
   (e) estimating activation patterns of the electrical activity within the three dimension space of the heart, by comparing and minimizing the difference between the collected signals and source model generated signals over the same sensor positions and over a certain time epoch, and
   (f) displaying the estimated activation patterns within the three dimension space of the heart.

2. An apparatus for imaging of electrical activities of a heart within a body, comprising a plurality of sensors for detecting signals over a part of a surface of the body, a part of the surface of the heart within the body, or a part of a surface out of the body, means for collecting the detected signals, means for determining positions of the sensors, means for determining geometry information of the heart within the body and of the torso, means for constructing an electrical source model of the heart, which comprises a three dimension distribution of current dipoles or monopoles or electric potentials, or a computer heart model incorporating physiological a priori information that simulates the physiological and pathophysiological processes of the heart, means for estimating activation patterns within the three dimension volume of the heart, by comparing and minimizing the difference between the detected signals and source model generated signals over the same sensor positions over a certain time epoch, and means for displaying the estimated activation patterns within the three dimension volume of the heart.

3. A method of imaging of electrical activities in a system comprising the steps of:
   (a) collecting signals over a part of a surface of the system or over a part of a surface out of the system using a plurality of sensors and a data acquisition unit,
   (b) determining positions of the sensors,
   (c) determining geometry information of the system,
   (d) constructing an electrical source model of the system,
   (e) estimating electrical source distribution and excitation sequence within the three dimension space of the system, by comparing and minimizing the difference between the collected signals and source model generated signals over the same sensor positions and over a certain time epoch, and
   (f) displaying the estimated electrical source distribution and excitation sequence within the three dimension space of the system.

4. The method of claim 3 wherein said steps (a) to (f) are repeated for sequential time epochs.

5. The method of claims 3 wherein the system is a biological system.

6. The method of claim 3 wherein the electrical activities originate in the heart.

7. The method of claim 3 wherein the electrical activities originate in the brain.

8. The method of claim 6 wherein the electrical source model comprises a three dimension distribution of current dipoles or monopoles or electric potentials.

9. The method of claim 6 wherein the electrical source distributions in the three dimension of the heart are estimated by using weighted minimum norm strategies.

10. The method of claim 6 wherein the electrical source distributions in the three dimension of the heart are estimated by means of weighted minimum norm strategies, and further enhanced by recursive weighting algorithm, in which the weighting matrix $W_k$ is updated by taking the product of $W_{k-1}$ with the diagonal current matrix from the preceding step:

$$W_k = W_{k-1} \cdot \text{diag}(X_1^{k-1} X_2^{k-1} \ldots X_n^{k-1})$$

where each diagonal element of W corresponds to one element of the source.

11. The method of claim 5 wherein the electrical source model is constructed in such a way that a priori knowledge on the properties of physiological excitation processes are incorporated, including cellular action potentials, excitation rules that determine when and whether an excitable cell is to be activated as responding to the inputs from the adjacent excitable cells, models of the excitable membrane as described by differential equations, and inhomogeneity of a biological system.

12. The method of claim 6 wherein the electrical source model is constructed in such a way that a priori knowledge on the properties of cardiac physiological and pathological excitation and repolarization processes are incorporated, including cellular action potentials, excitation rules, and inhomogeneity properties of myocardium.

13. The method of claim 7 wherein the electrical source model is constructed in such a way that a priori knowledge on the properties of brain physiological and pathological excitation processes are incorporated, including properties of neuronal cellular action potentials, excitation rules of the neural electrical activity, and inhomogeneity properties of the brain tissue.

14. The method of claim 3 further including a step of determining the initial values of the parameters for the electrical source model, using artificial neural networks.

15. An apparatus for imaging of electrical activities in a three dimensional biological system, comprising a plurality of sensors for detecting signals over a part of a surface of the biological system or over a part of a surface out of the biological system, means for collecting the detected signals, means for determining positions of the sensors, means for determining geometry information of the system, means for constructing an electrical source model of the system, means for estimating electrical source distribution and excitation sequence within the system, by comparing and minimizing the difference between the detected signals and source model generated signals over the same sensor positions over a certain time epoch, and means for displaying the estimated electrical source distribution and excitation sequence within the three dimension space of the system.

16. The apparatus of claim 15 further including means for imaging of the electrical activities for sequential time epochs.

17. The apparatus of claim 15 wherein the means for collecting the signals include an array of bioelectric electrodes.

18. The apparatus of claim 15 wherein the plurality of sensors include an array of magnetic sensors.

19. The apparatus of claim 15 wherein the plurality of sensors includes an array of magnetic sensors and an array of electrodes.

20. The apparatus of claim 15 wherein it is used together with a catheter, guiding catheter ablation of cardiac arrhythmia.

* * * * *